United States Patent
Müller et al.

(10) Patent No.: US 11,578,319 B2
(45) Date of Patent: Feb. 14, 2023

(54) RAPID PURIFICATION OF HIGH QUALITY NUCLEIC ACIDS FROM BIOLOGICAL SAMPLES

(71) Applicant: BIOECHO LIFE SCIENCES GMBH, Cologne (DE)

(72) Inventors: Markus Müller, Dormagen (DE); Jörg Hucklenbroich, Tente (DE)

(73) Assignee: BIOECHO LIFE SCIENCES GMBH, Cologne (DE)

(*) Notice: Subject to any disclaimer, the term of this patent is extended or adjusted under 35 U.S.C. 154(b) by 567 days.

(21) Appl. No.: 16/610,932

(22) PCT Filed: May 7, 2018

(86) PCT No.: PCT/EP2018/061695
§ 371 (c)(1),
(2) Date: Nov. 5, 2019

(87) PCT Pub. No.: WO2018/202911
PCT Pub. Date: Nov. 8, 2018

(65) Prior Publication Data
US 2020/0056169 A1 Feb. 20, 2020

(30) Foreign Application Priority Data
May 5, 2017 (LU) .................................. 100193

(51) Int. Cl.
*C12Q 1/68* (2018.01)
*C12N 15/10* (2006.01)

(52) U.S. Cl.
CPC ................ *C12N 15/1017* (2013.01)

(58) Field of Classification Search
CPC ................................................ C12Q 1/68
(Continued)

(56) References Cited

U.S. PATENT DOCUMENTS

2008/0166703 A1* 7/2008 Himmelreich .......... C07H 1/08
536/25.41
2009/0047724 A1* 2/2009 Hillebrand ......... C12N 15/1003
435/219

(Continued)

FOREIGN PATENT DOCUMENTS

DE 19856064 6/2000
EP 3135769 A1 * 3/2017

(Continued)

OTHER PUBLICATIONS

Japanese Office Action for App. No. JP2020-512087, dated Sep. 15, 2021, 9 pages.

(Continued)

*Primary Examiner* — Aaron A Priest
(74) *Attorney, Agent, or Firm* — Riverside Law, LLP

(57) ABSTRACT

This invention relates to a method for the purification of nucleic acids, preferably DNA, from biological samples, comprising the steps (a) optional lysis of said sample, (b) optional heat incubation of said sample, (c) enzymatic digestion of non-nucleic acid components in the product of step (a) or (b), (d) heat inactivation of one or more enzyme(s) used in step (c), (e) transfer of the product of step (d) onto a resin capable of retaining non-nucleic acid components, while the nucleic acids pass through the resin, thereby purifying the nucleic acids.

19 Claims, 3 Drawing Sheets

Figure 1:
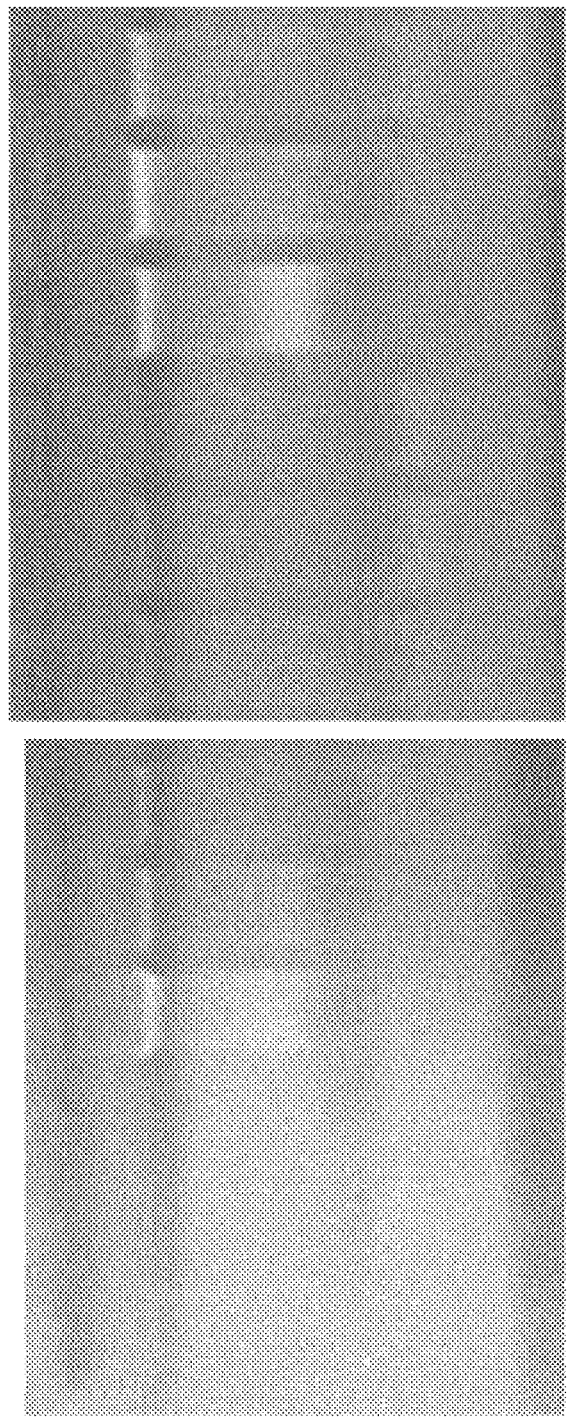

(58) Field of Classification Search
USPC .......................................................... 435/6.1
See application file for complete search history.

(56) References Cited

U.S. PATENT DOCUMENTS

| 2009/0081678 | A1* | 3/2009 | Ryan ................. C12N 15/1003 536/25.4 |
| 2010/0143302 | A1 | 6/2010 | Havenga |
| 2011/0189654 | A1* | 8/2011 | Himmelreich ....... A61K 9/2009 435/6.12 |
| 2013/0030165 | A1 | 1/2013 | Fabis |
| 2013/0053254 | A1* | 2/2013 | Hollander .......... C12N 15/1003 204/461 |

FOREIGN PATENT DOCUMENTS

| EP | 3135769 A1 | 3/2017 |
| JP | 2013528786 A | 7/2013 |
| JP | 2013530697 A | 8/2013 |
| WO | 2011124703 A1 | 10/2011 |
| WO | 2011124709 A1 | 10/2011 |
| WO | 2011157683 A1 | 12/2011 |

OTHER PUBLICATIONS

European Patent Office Communication pursuant to Article 94(3) EPC for App. No. EP18726931.1, dated Sep. 15, 2021, 6 pages.

Yamada A et al: "Molecular cloning of a glycosylphosphatidylinositol-anchored molecule CDw108", The Journal of Immunology, Williams & Wilkins Co, US, vol. 162, Apr. 1, 1999 (Apr. 1, 1999), pp. 4094-4100, XP002123609, ISSN: 0022-1767.

Wilson W J et al: "A multiplexed PCR-coupled liquid bead array for the simultaneous detection of four biothreat agents", Molecular and Cellular Probes, Academic Press, London, GB, vol. 19, No. 2, Apr. 1, 2005 (Apr. 1, 2005), pp. 137-144, XP004725276, ISSN: 0890-8508, DOI: 10.1016/J.MCP.2004.10.005.

\* cited by examiner

RAPID PURIFICATION OF HIGH QUALITY NUCLEIC ACIDS FROM BIOLOGICAL SAMPLES

CROSS-REFERENCE TO RELATED APPLICATIONS

This application is the U.S. national phase application filed under 35 U.S.C. § 371 claiming benefit to International Patent Application No. PCT/EP2018/061695, filed on May 7, 2018, which is entitled to priority under to Luxembourg Patent Application No. 100193, filed May 5, 2017, the entire disclosures of which are incorporated by reference herein as if set forth herein in their entirety.

FIELD OF THE INVENTION

The present invention refers to a method for isolating nucleic acids from a sample, comprising the following steps: (a) optional lysis of said sample, (b) optional heat incubation of said sample, (c) enzymatic digestion of non-nucleic acid components in the product of step (a) or (b), (d) heat inactivation of one or more enzyme(s) used in step (c), (e) transfer of the product of step (d) onto a resin capable of retaining non-nucleic acid components, while the nucleic acids pass through the resin, thereby purifying the nucleic acids.

BACKGROUND OF THE INVENTION

The isolation of genomic DNA from tissue, cell culture cells and blood samples for molecular analyses is a commonly applied technique. Various protocols for this application have been developed over the past several decades within the scientific community. The commonly most used methodology is the binding of nucleic acids to silica surface in the presence of highly concentrated chaotropic salts and organic solvents.

The bound nucleic acid is washed with several washing buffers also containing chaotropes with or without added organic solvents to be finally eluted from the silica surface under low-salt buffer conditions. The silica-based purification principle is used in more than 90% of the kits commercially available on the market. DNA purified by this method is used in molecular downstream applications like polymerase chain reaction (PCR), cloning, sequencing, etc. The drawbacks of silica-based purifications are as follows: The high-salt and often organic solvent-containing buffers used in the binding and elution of DNA from silica surface exhibit the risk to be carried over into the DNA-containing eluate and therewith compromise or even inhibit downstream applications, especially sensitive PCR-based assays, but also other enzymatic reactions like ligation and sequencing reactions. Additionally, the underlying bind-wash-elute principle of so called positive chromatography leads to low recoveries of the DNA present in the sample. The procedure is a multi-step operation and generates large amounts of plastic waste and hazardous waste solutions.

Due to the lack of innovative momentum in the field of nucleic acid extractions over the last decades, this method is still the market leading routine despite the availability of modern separation matrices and filters just as new enzyme formulations and detergents that can, if combined in novel combinations and set-ups, create innovative and improved methods for the isolation of nucleic acids.

One promising approach to overcome the disadvantages of the positive chromatography principle is to apply the negative chromatography principle, in which the lead substance—in this case a nucleic acid like DNA and/or RNA—is not bound to a matrix but instead the contaminants, inhibitors and undesired cell residues, while the DNA leaves the column in a purified state. The reversion of the principle leads to a much faster processing with much less steps involved compared to bind-wash-elute-protocol. This leads to a reduction of more than 70% of the plastic waste that incurs in a conventional nucleic acid kits produce. At the same time, the usage of only aqueous buffers and non-toxic reagents avoids the generation of hazardous waste chemicals as well. One of the biggest advantages of negative compared to positive chromatography (where the target DNA is bound) is the well-known higher relative recovery of the target molecules. While bind-wash-elute purifications pose the risk of target molecule losses during the binding, washing and elution steps, negative chromatography typically recovers more than 90% of the target as the purification is not dependent on a binding event.

The principle of negative chromatography by itself is not new and has been employed and commercialized already in some "clean-up" procedures for nucleic acids. Also there are a few vendors that sell DNA purification kits using one-step procedures, but all of these products deliver low quality DNA preparations, meaning colored eluates, low ratios of $OD_{260}/OD_{230}$ and/or $OD_{260}/OD_{280}$, eluates containing UV-absorbing stabilizers (e.g. azide) or inhibitor-containing eluates etc., due to crude and poorly developed pre-column process steps.

The key to employ negative chromatography as an high quality purification methodology for nucleic acids lies in the pre-column steps to efficiently and completely disintegrate the respective samples, from which the nucleic acid is intended to be isolated (e.g. tissue, blood, cell culture cells, bacteria, plant cells, etc.).

The approach to develop sample purification methodologies that avoid the use of environmental harmful high salt solutions and organic solvents faces the challenge to fully disintegrate the sample or specimen without the help of chaotropic salt solutions. Those denature proteins, thereby destabilize cell membranes, and facilitate the disintegration of cell walls and -membranes. Another important effect of the denaturation of proteins of chaotropic salts, which is the cause for their toxicity as well, is the inhibition of nuclease activities like RNases and DNases. These both main activities of chaotropic salts determined their use in nucleic acid purification methods.

The attempt to eliminate the use of these chemicals poses the challenge to achieve cell membrane disintegration and inhibition of nucleases in different approaches. Similar attempts have been made and published but resulting in only low quality or low yield methods. For example, a method for purification of nucleic acids including a preparative step before separation of nucleic acids is disclosed in WO 2011/124703 A1.

However, there is still a need in reliable, improved and alternative ways of preparation of a biological sample before separation of nucleic acids. Accordingly, the technical problem underlying the present application is to comply with this need.

SUMMARY OF THE INVENTION

The inventors of the present application unexpectedly found conditions that improve the quality and increase the amount of nucleic acids isolated from biological samples as illustrated in the description, the examples and the claims.

These conditions are characterized by use of novel proteases, use of $(NH_4)_2SO_4$, increased SDS and/or $SrCl_2$ concentrations, initial heat inactivation of nucleases and/or the transfer of a lysed biological sample with elevated temperature onto a resin.

The present invention discloses an approach that enables the use of negative chromatography to purify DNA in high quality and suitable for all molecular downstream applications. This improved procedure speeds nucleic acid purification dramatically up, reduces the number of handling steps significantly and increases the yield of sample-contained nucleic acids significantly. At the same time, it is not prone to deliver false-negative results due to co-elution of highly concentrated salts or organic solvents into the DNA-eluate to compromise or inhibit downstream analyses like PCR and next generation sequencing (NGS).

The present invention relates to a method for isolating nucleic acids from a sample, comprising the following steps:
(a) optional lysis of said sample,
(b) optional heat incubation of said sample,
(c) enzymatic digestion of non-nucleic acid components in the product of step (a) or (b),
(d) heat inactivation of one or more enzyme(s) used in step (c),
(e) transfer of the product of step (d) onto a resin capable of retaining non-nucleic acid components, while the nucleic acids pass through the resin,
thereby purifying the nucleic acids.

In a preferred embodiment of the present invention, the heat incubation of step (b) is carried out at a temperature between 75° C. and 95° C. for 1 to 20 min, more preferably for 2 to 10 min.

In the method according to the present invention, a detergent is preferably added during step (a) to a final concentration of at least or about 10 mM SDS, at least or about 20 mM SDS, at least or about 30 mM SDS, at least or about 40 mM SDS, at least or about 50 mM SDS, at least or about 60 mM SDS, at least or about 100 mM SDS, at least or about 150 mM SDS, at least or about 200 mM SDS, at least or about 250 mM in the product of step (a).

The heat incubation of step (b) in the method according to this invention is preferably carried out at least 1 min, at least 5 min, at least 10 min, at least 15 min or at least 20 min.

In a preferred embodiment of the present invention, one or preferably more enzyme(s) is/are used in step (c) for the enzymatic digestion, wherein the one or more enzyme(s) is/are lytic enzyme(s), preferably selected from the group consisting of proteases, lipases, cellulases, hydrolases, chitinases, amylases and glucanases, wherein hydrolases are not nucleases.

In a more preferred embodiment of the present invention, the lytic enzyme(s) of step (c) is/are one or more, preferably more, proteases selected from the group consisting of protease from *Bacillus licheniformis*, protease from *Bacillus* spec., protease from *Staphylococcus aureus*, protease from *Bacillus amyloliquefaciens*, protease from *Coprinus* spec. and protease from *Aspergillus oryzae*.

The enzymatic digestion of step (c) according to the method of the present invention is preferably carried out between 15° C. and 70° C. for 5 min to 120 min.

Ammonium salt(s) and/or sulfate salt(s), preferably ammonium sulfate, is/are preferably added in step (a), more preferably to a final concentration of at least 70 mM ammonium sulfate in the method according to the present invention. Alternatively or additionally, an ammonium salt, such as ammonium chloride can be added in step (a). In particular, at least 5 mM, 10 mM, 25 mM, 50 mM, 100 mM, 120 mM, 150 mM, 180 mM, 200 mM, 225 mM, 250 mM, 275 mM, 300 mM, 350 mM or more can be added in step (a). For example, 155 mM ammonium chloride can be added in step (a). It is also envisioned that 150 mM ammonium chloride can be added in step (a).

The product of step (d) according to the method of the present invention is preferably added with a temperature between 60° C. and 95° C. onto the resin of step (e) according to the method of the present invention.

Preferably, $SrCl_2$ and/or $BaCl_2$ is/are added to a final concentration of at least 400 mM to the product of step (d) before transfer onto the resin in step (e).

Preferably, a chelating agent, more preferably EDTA, is added at step (a) according to the method of the present invention.

The sample according to the method of the present invention preferably is a feces sample, blood sample, urine sample, tissue sample and/or body fluid sample.

The nucleic acid of the present invention is preferably DNA and/or RNA, more preferably DNA.

The centrifugation step in step (e) according to the method of the present invention preferably is executed at 400 g to 3000 g for 0.5 min to 5 min, more preferably for about 1 min. The centrifugation step in step (e)—according to the method of the present invention—is preferably executed at 400 g to 3000 g for 0.5 min to 5 min, more preferably for about 1 min, after transfer of the product of step (d) onto the resin.

The resin according to the method of the present invention is preferably a size-exclusion resin with exclusion limits in the range of 20 to 2000 bp of single and/or double stranded nucleotide strands.

The resin according to the method of the present invention preferably is incorporated into a centrifugation column. The resin according to the method of the present invention can thus be incorporated into a spin column.

The resin according to the method of the present invention is preferably centrifuged at least 1 min at at least 300 g before the lysate of step (d) of the present invention is added onto the resin or the spin column in step (e) of the present invention.

The lysate according to the method of the present invention of step (c) or step (d) is preferably cleared from precipitates by centrifugation of the lysate before it is applied onto the resin in step (e), more preferably by centrifugation at 10.000 g for 1 to 5 min.

FIGURE LEGENDS

FIG. 1: Influence of heat inactivation step, EDTA and high SDS concentrations in lysis buffer. Samples were treated as described in Example 1. The resulting DNA was subjected to agarose gel electrophoresis.

Figure 2:
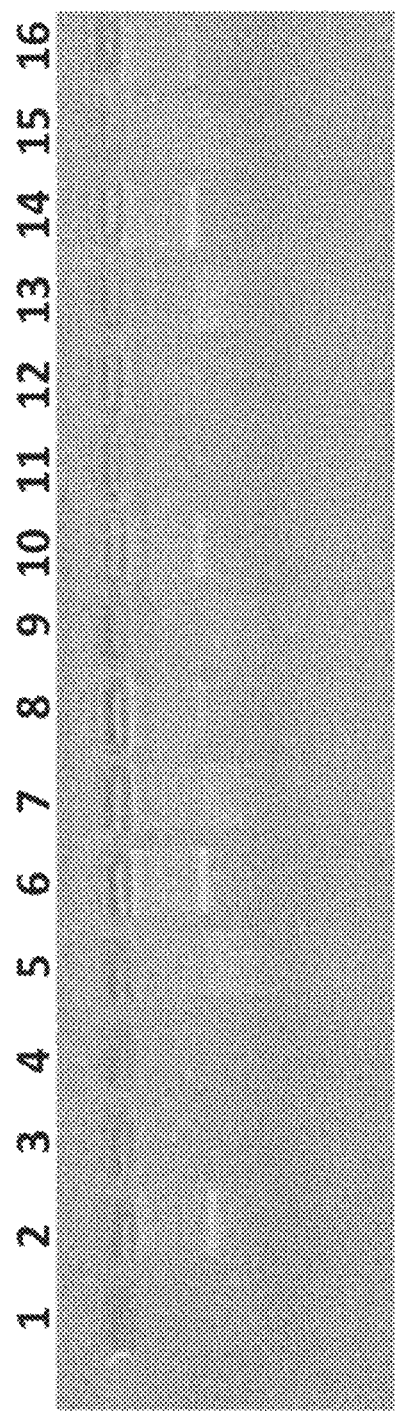

FIG. 2: Influence of ammonium sulfate in lysis buffer. Samples were treated as described in Example 2. The resulting DNA was subjected to agarose gel electrophoresis.

Figure 3:
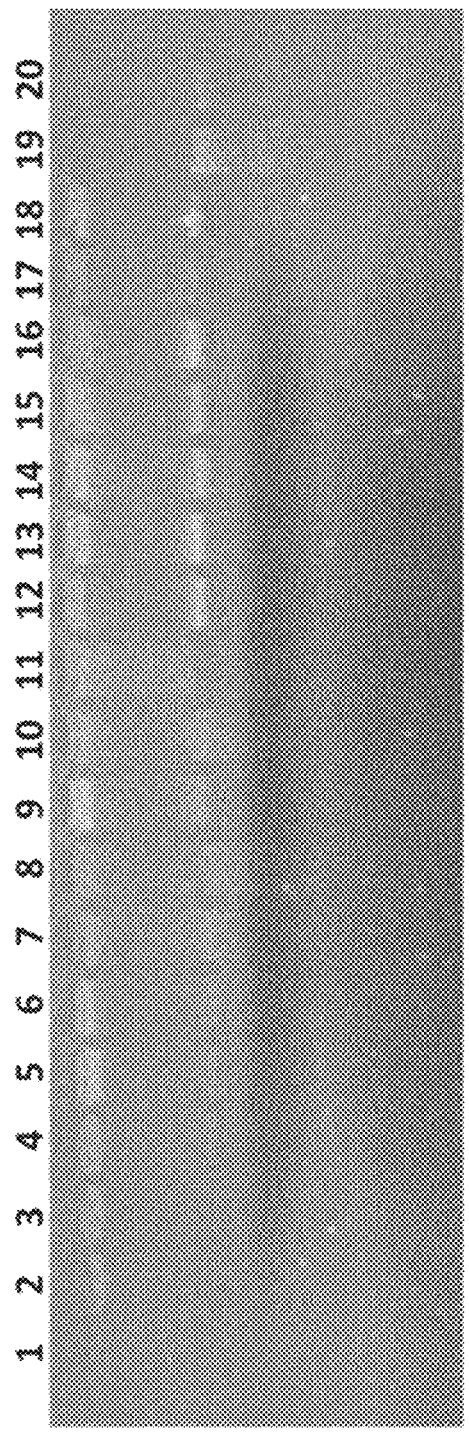

FIG. 3: Influence of new proteases. Samples were treated as described in Example 3. The resulting DNA was subjected to agarose gel electrophoresis.

DETAILED DESCRIPTION

Definitions

As used herein, the term "nucleic acid" comprises any type of DNA or RNA as well as a mixture of DNA and RNA of any type.

As used herein, "positive chromatography" herein refers to a method of enriching a compound by retaining the compound to be enriched in a chromatography device, wherein undesired contaminants, inhibitors and other components are washed away and the compound to be enriched is eluted in a final step. "Negative chromatography" herein refers to a method of enriching a compound by retaining the undesired contaminants in a chromatography device and/or a resin, while the compound to be enriched passes the chromatography device.

As used herein, the term "non-nucleic acid components" comprises all non-nucleic acid compounds in a solution, especially those that compromise or even inhibit subsequent or downstream applications like PCR, cloning, ligation and/or sequencing of nucleic acids. Especially comprised by the term "non-nucleic acid components" are proteins, salts, chaotropic agents, detergents, organic or inorganic solvents, dyes, metabolites, sample debris, low molecular molecules (e.g. nucleotides etc.) and/or PCR inhibitors.

As used herein, the term "resin" comprises an insoluble matrix or medium capable of interacting with binding partners. Typically, a resin is used in a chromatographic procedure, wherein the resin retains different components depending on their characteristics to a different extent and thereby separates the different components of the solution or mixture.

A "biological sample" as used herein, refers to any biological material containing nucleic acids, preferably DNA. In one embodiment, biological samples comprise cells and/or cell-free nucleic acids from bacteria, virus, protozoa, chromista, fungi, plants and/or animals. In another embodiment, the biological samples are isolated from fungi, plants and/or animals, but may contain biological samples consisting of cells from bacteria, protozoa, chromista, fungi, plants and/or animals. In one embodiment, animal refers to vertebrates, preferably tetrapods, fish, and/or birds, more preferably mammals and even more preferably cows, cats, dogs, horses, pigs, humans. In another preferred embodiment of the invention, animals refer to animals for production/livestock. In an additional embodiment of the invention, the biological sample refers to a forensic case sample.

In preferred embodiments, the biological sample is a body fluid sample, an environmental sample, a cell culture sample, a bone marrow sample, a sewage sample, a food sample, a milk sample, a forensic sample, a biological molecule production sample, a protein preparation sample, a lipid preparation sample, a carbohydrate preparation sample, and any combination thereof, wherein, optionally, the body fluid sample is one of a blood sample, a serum sample, an amniotic fluid sample, a semen sample, a lymphatic fluid sample, a cerebrospinal fluid sample, a nasopharyngeal wash sample, a sputum sample, a mouth swab sample, a throat swab sample, a nasal swab sample, a bronchoalveolar lavage sample, a bronchial secretion sample, and an urine sample.

DETAILED DESCRIPTION OF THE EMBODIMENTS

The method for isolating nucleic acids from a sample of the present invention comprises the following steps:
(a) optional lysis of a sample,
(b) optional heat incubation of said sample,
(c) enzymatic digestion of non-nucleic acid components in the product of step (a) or (b),
(d) heat inactivation of one or more enzyme(s) used in step (c),
(e) transfer of the product of step (d) onto a resin capable of retaining non-nucleic acid components, while the nucleic acids pass through the resin, thereby purifying the nucleic acids.

Certain different embodiments including preferred embodiments of the invention will be described in the following detailed description of the invention. Although all nucleic acids are envisaged by this invention, the purification of DNA is preferred.

In a preferred embodiment of the present invention, the resin is one used for size exclusion chromatography (SEC). Preferably a water-based mobile phase, such as water, an aqueous organic solvent or an aqueous buffer/solution is used as mobile phase. SEC is a chromatographic method, wherein molecules are separated based on their size, or more precisely based on their hydrodynamic volume. Commonly, a solid matrix is able to form a gel bed, when suspended in an aqueous medium. Components of such a solid matrix comprise Sephadex, Sephacryl, crosslinked agarose, silica-based materials, diatomaceous earth, polystyrene/divinyl benzene, and/or ceramic hydroxy apatite. One or more components may also be mixed. The one or more component is suspended in a buffer and packed in the hollow body of a column. Columns may be made of glass, plastic, Teflon or any other material that neither reacts with the mobile phase nor the analyte. The bead or amorphous particle size can range from 1 µm to 500 µm, preferably 25 µm to 400 µm, average diameters, depending on volume and debris concentration loaded onto the respective resin or column beds.

The sample to be purified is then applied to the gel's bed upper surface, and allowed to pass through the gel, either by gravity or forced by centrifugation, vacuum or pressure. Within this invention, centrifugal forces are preferably applied to move the mobile phase down the column, wherein the columns are spun in a centrifuge (so-called spin column technique, "centrifugation column"). Due to the nature of the resin, pores of a certain size exist inside the gel. Small molecules are able to penetrate the pores, and therefore move through the resin more slowly, being retained as they pass down the column, while large molecules cannot penetrate the pores and move down the column more quickly. After having passed the column, the mobile phase (now referred to as "eluate"), containing the purified nucleic acid, is then collected at the outlet of the column. To retain the resin within the hollow body of the column, a porous frit, filter, fleece or membrane is preferably placed between the outlet of the column and the solid matrix, wherein nucleic acids of all sizes may pass said frit, filter, fleece or membrane.

In SEC, the size exclusion limit defines the molecular weight or length of a nucleic acid, where molecules are too large to be trapped in the stationary phase/the resin. The size exclusion limit of a resin is defined by the composition of the resin and can be influenced by particle size, the type of resin and the degree of crosslinking. In one embodiment of the invention, the size exclusion limit of the resin is between 1 and $10^6$ base pairs (bp). In a preferred embodiment, the size exclusion limit is between 5 and 10000 bp and in a more preferred embodiment, the size exclusion limit is in the range of 20 to 2000 bp. As used herein, the units "base pairs" (bp) and "nucleotides" (nt) can be used interchangeably.

The resin is preferably incorporated into a column. This column comprises a hollow body having an inlet and an outlet, the hollow body comprises a solid matrix providing size excluding properties. Preferably, it additionally comprises a porous frit, filter, fleece or membrane, preferably allowing nucleic acids of any size to pass, placed between the outlet and the resin to retain the resin within the column. The column optionally comprises a non-porous ring placed between the porous frit, filter, fleece or membrane and the resin, sealing the outer area of the frit, filter, fleece or membrane, to prevent the mobile phase from entering the frit without passing the resin. Also, optionally, the column comprises at least one removable closing device to seal the inlet and/or the outlet of the chromatographic unit. Further optionally, the column comprises at least one collection tube to collect the mobile phase (eluate) after having passed the resin. The material of the column may be selected from the group consisting of glass, polypropylene, polycarbonate or polyethylene.

The lysis of a biological sample like, e.g., feces sample, blood sample, tissue sample and/or body fluid sample is crucial for the subsequent steps of this purification protocol. However, for some samples like, e.g., urine samples, a lysis is optional. Although a lysis step might be optional, the heat incubation step (b) might still be necessary. Essential for a complete lysis of a sample is the lytic enzyme selection and activity, detergent and respective concentration, the incubation time and the incubation temperature.

The lysis step can include the use of a buffer substance in which the detergent, chelating agent or other substances/components described herein can be added e.g. in step (a) can be solved. The buffer substance can be any buffer substance known to the skilled artesian. Non-limiting examples include TRIS, such as TRIS-HCl, tartrate buffer, borate buffer, carbonate buffer, citrate buffer, HEPES, HPPS or any ammonia buffer. It is envisioned that the buffer substance can be added in a concentration of 5 mM, 10 mM, 15 mM, 20 mM, 25 mM, 50 mM, 75 mM, 100 mM, 125 mM, 150 mM, 175 mM, 200 mM, 250 mM or more during step (a). For example, 25 mM of the buffer substance such as TRIS/HCl can be added during step (a). It is also envisioned that 50 mM of the buffer substance such as TRIS/HCl can be added during step (a). Additionally or alternatively, 50 mM of the buffer substance, such as tartaric acid, boric acid, carbonic acid or citric acid, can be added during step (a). Various detergents suitable for sample lysis are available. An important feature of those useful in lysis of a biological sample for nucleic acid purification is the capability to lyse cells and as an optional feature to inhibit the activity of nucleases. In one embodiment, the detergent is sodium dodecyl sulfate (SDS), Triton X-100, Triton X-114, NP-40, Brij-35, Brij-58, Tween 20, Tween 80, octyl glucoside, octyl thioglucoside, 3-[(3-cholamidopropydim-ethylammonio]-1-propanesulfonate (CHAPS) and/or 3-[(3-cholamidopropyl)dimethylammonio]-2-hydroxy-1-propanesulfonate (CHAPSO). The detergent can also be lithium dodecyl sulfate (LiDS). In a preferred embodiment, the detergent used for the lysis of the biological sample is SDS and/or its derivatives. Thus, the detergent used for the lysis of the biological sample can be lithium dodecyl sulfate.

In one embodiment, the concentration of the detergent is at least 1 mM. In another embodiment, the concentration is at most 100 mM SDS. In yet another embodiment, the concentration is at least 10 mM, 20 mM, 30 mM, 40 mM, 50 mM, at least 60 mM, at least 100 mM, at least 150 mM, at least 200 mM or at least 300 mM. In a preferred embodiment, the concentration of the detergent is at least 100 mM. In another preferred embodiment, the concentration of the detergent is more than 100 mM (excluding 100 mM). In a more preferred embodiment, a detergent is added during step (a) to a final concentration of at least 60 mM SDS, preferably at least 100 mM SDS, in the product of step (a). Thus, the detergent such as e.g. SDS can be added during step (a) to a final concentration of at least 110 mM, 120 mM, 130 mM, 140 mM, 150 mM, 160 mM, 170 mM, 180 mM, 190 mM, 200 mM, 210 mM, 220 mM, 230 mM, 240 mM, 250 mM, 260 mM, 270 mM, 280 mM, 290 mM, 300 mM, 400 mM, 500 mM or more in the product of step (a).

In one embodiment, the concentration of lithium dodecyl sulfate is at least 1 mM. In another embodiment, the concentration is at most 300 mM lithium dodecyl sulfate. In yet another embodiment, the concentration of lithium dodecyl sulfate is at least or about 10 mM, at least or about 20 mM, at least or about 30 mM, at least or about 40 mM, at least or about 50 mM, at least or about 60 mM, at least or about 100 mM, at least or about 150 mM, at least or about 200 mM, at least or about 250 mM or at least or about 300 mM. In a preferred embodiment, the concentration of the detergent such as lithium dodecyl sulfate is about 100 mM.

In one embodiment, the concentration of SDS is at least 1 mM. In another embodiment, the concentration is at most 300 mM SDS. In yet another embodiment, the concentration of SDS is at least or about 10 mM, is at least or about 20 mM, is at least or about 30 mM, is at least or about 0 mM, is at least or about 50 mM, at least or about 60 mM, at least or about 100 mM, at least or about 150 mM, at least or about 200 mM, at least or about 250 mM or at least or about 300 mM. In a preferred embodiment, the concentration of the detergent such as SDS is about 100 mM.

It is further envisioned that the lysis step does not include the use of an acid such as an strong acid. For example, the lysis step may not include the use of sulfuric acid ($H_2SO_4$). It is further envisioned that the method as described herein is performed in the absence of $H_2SO_4$. Thus, steps (a)-(e) of the method of the present invention can all be performed without the addition of $H_2SO_4$.

Another important factor of an efficient lysis is the incubation time. The lysis can be carried out for any suitable amount of time. The lysis can be carried out for at least 1 min, at least 2 min, at least 5 min, at least 10 min, at least 15 min, at least 20 min, at least 30 min, at least 45 min or at least 60 min. The incubation time may depend on the type of the biological sample. In other embodiments, the incubation time is in the range of 1 to 20 min, in a preferred embodiment 2 to 15 min and in a more preferred embodiment in the range of 2 to 10 min.

Another important factor of an efficient lysis is the pH at which lysis takes place. The lysis can be carried out for at any suitable pH. For example, the lysis may be performed at a pH between 5 and 15. The pH can also be between 7 and 13. The pH may also be between 7 and 10, 7 and 9 or 7 and 8.5. The pH may also be between 8.0-8.5. Preferably the pH is adjusted with an acid such as HCl. The inactivation of nucleases may be facilitated by an optional heat incubation step (b). This optional heat incubation step is carried out at a temperature between 75° C. and 95° C. In a further preferred embodiment of the present invention, the heat incubation of step (b) is carried for 1 to 20 min, more preferably for 2 to 10 min. In a more preferred embodiment of the present invention the heat incubation of step (b) is carried out at a temperature between 75 and 95° C., even more preferably at a temperature between 80 and 95° C., for 1 to 20 min, even more preferably for 2 to 10 min.

Another essential factor contributing to a fast and efficient preparation of the biological sample for the subsequent separation of nucleic acids from non-nucleic acid components on a resin is the enzymatic digestion of those non-nucleic acid components. Enzymatic treatment of non-nucleic acid components decreases the (hydrodynamic) size of non-nucleic acid components and thereby increases the interaction with the resin. Hence, non-nucleic acid components are retained to a stronger amount by the resin and the separation of nucleic acid from non-nucleic acid components is improved. In one embodiment of the invention, the enzymes, preferably lytic enzymes, are selected from the group consisting of proteases, lipases, cellulases, hydrolases, chitinases, amylases and glucanases, wherein hydrolyses are not nucleases. The group of hydrolases comprises nucleases, but as the purpose of the method of this invention is to isolate nucleic acids, the term "hydrolases" as used herein does not comprise nucleases. Every combination of one or more enzymes of those enzymatic groups is encompassed in this invention. In a preferred embodiment of the invention, the one or preferably more enzyme(s) is/are used in step (c) for the enzymatic digestion, wherein the one or more enzyme(s) is/are lytic enzyme(s), preferably selected from the group consisting of proteases, lipases, cellulases, hydrolases, chitinases, amylases and glucanases.

In a preferred embodiment, proteases are used for the digestion of proteinaceous non-nucleic acid components. In general, one or more different proteases may be used for the enzymatic digestion. In a more preferred embodiment of the invention, one or more protease(s) is/are used in step (c) and the one or more protease(s) is/are selected from the group consisting of protease from *Bacillus licheniformis*, protease from *Bacillus* spec., protease from *Staphylococcus aureus*, protease from *Bacillus amyloliquefaciens*, protease from *Coprinus* spec. and protease from *Aspergillus oryzae*. In another embodiment, one or more protease(s) is/are used in step (c) and the one or more protease(s) is/are selected from the group consisting of protease from *Bacillus licheniformis*, protease from *Bacillus* spec., protease from *Staphylococcus aureus*, protease from *Bacillus amyloliquefaciens*, and protease from *Aspergillus oryzae*. The selection of different combinations of proteases depends on the biological sample.

The incubation time and the temperature, at which the enzymatic digestion takes place, decide as well the efficiency of the enzymatic digestion. In one embodiment, the incubation time for the enzymatic digestion is in the range of 1 to 240 min, preferably in the range of 5 to 120 min. The temperature, at which the enzymatic digestion is carried out, is in one embodiment in the range of 4 to 95° C. In another embodiment, the temperature is in the range of 4 to 55° C., in the range of 55 to 65° C. or in the range of 65 to 95° C. In a preferred embodiment, the incubation temperature is in the range of 15 to 70° C. In a more preferred embodiment, the incubation temperature is in the range of 15 to 65° C. The person skilled in the art can easily determine the time and temperature needed for an efficient enzymatic digestion by using standard procedures known in the art.

Preferably, the enzymes used in step (c) may be inactivated by heating of the product of step (c). This heat inactivation prevents interferences with subsequent applications after purifying the nucleic acids. In one embodiment, the product of step (c) is heated to a temperature in the range of 75 to 95° C., preferably of 90 to 95° C. In another embodiment, the product of step (c) is heated for 2 to 10 min, preferably for 5 to 10 min. In another embodiment, the product of step (c) is heated to a temperature in the range of 75 to 95° C., preferably 90 to 95° C., for 2 to 10 min, preferably 5 to 10 min.

In a preferred embodiment, the enzymatic digestion of step (c) is carried out between 15° C. and 70° C. for 5 min to 120 min, optionally followed by the heat inactivation of the one or more enzyme(s) used in step (c) at 75 to 95° C. for 2 to 10 min.

To improve the quality and to prevent degradation of nucleic acids, preferably DNA, isolated by means of this invention, "DNA stabilizers" may be added at step (a) in certain embodiments of the invention. In one embodiment, ammonium salt(s) such as ammonium chloride and/or sulfate salt(s) are used as DNA stabilizers and added at step (a). Another DNA stabilizer may be calcium chloride ($CaCl_2$), which can additionally or alternatively be added at step (a). In a preferred embodiment, ammonium sulfate is used as DNA stabilizer and added to the biological sample of step (a). In one embodiment, the concentration of the DNA stabilizer is at least 1 mM, at least 5 mM, at least 10 mM, at least 50 mM, at least 70 mM, at least 100 mM, at least 150 mM, at least 180 mM, at least 200 mM, at least 250 mM, at least 500 mM or at least 1 M. In a preferred embodiment, the concentration of the DNA stabilizer is at least 70 mM. In another preferred embodiment, ammonium salt(s) such as ammonium chloride and/or sulfate salt(s), more preferably ammonium sulfate, is/are added in step (a), more preferably to a final concentration of at least 70 mM ammonium sulfate. Additionally or alternatively, 150 mM of ammonium chloride can be added during step (a). Additionally or alternatively, 155 mM of ammonium chloride can be added during step (a).

Further additives may be added in step (a) in certain embodiments of the invention. For example, calcium chloride can be added in step (a) in certain embodiments of the invention. It is envisioned that at least 0.5 mM, 1 mM, 2 mM, 3 mM, 4 mM, 5 mM, 6 mM, 7 mM, 8 mM, 9 mM, 10 mM or more $CaCl_2$ is added in in step (a). For example, 5 mM $CaCl_2$ is added in step (a).

The loading of the product of steps (c) or (d) onto the resin of step (e) can be carried out at a temperature in the range of 4 to 95° C. However, as a loading of the products of steps (c) or (d) at an elevated temperature onto the resin of step (e) has been shown beneficiary, it is preferred to add the product of steps (c) or (d) at an elevated temperature to the resin of step (e). In preferred embodiments, the temperature of the product of step (c) or (d) is in the range of 60 to 95° C., 70 to 95° C., 80 to 95° C., 90 to 95° C., 60 to 70° C., 60 to 80° C. or 70 to 80° C. before added to the resin of step (e). In a preferred embodiment, the product of step (d) is added with a temperature between 60 and 95° C. onto the resin of step (e).

Precipitation of undesired non-nucleic acid components can be facilitated by the addition of salts of alkali metals and/or salts of alkaline earth metals to the product of step (d) before transfer onto the resin of step (e). In principle any suitable salts of alkali metals and/or salts of alkaline earth metals can be used. In a preferred embodiment, $SrCl_2$ and/or $BaCl_2$ is/are added to the product of step (d) before transfer onto the resin of step (e). It is also envisioned that $SrCl_2$, $BaCl_2$, RbCl, CsCl, $CaCl_2$ is/are added to the product of step (d) before transfer onto the resin of step (e).

In one embodiment, the final concentration of the alkaline earth metal salt and/or the salt(s) of alkali metals is at least 1 mM, at least 5 mM, at least 10 mM, at least 50 mM, at least 100 mM, at least 150 mM, at least 180 mM, at least 200 mM, at least 250 mM, at least 400 mM, at least 500 mM at least 1 M, at least 1.25 mM, at least 1.5 mM, at least 1.75 mM, at least 2 mM, at last 2.25 mM, at least 2.5 mM, at least 2.75 mM, at least 3 mM or more. In a preferred embodiment, the concentration of the alkaline earth metal salt and/or the salt(s) of alkali metals is at least 400 mM. For example, the concentration of the alkaline earth metal salt and/or the salt(s) of alkali metals is at least 1.5 mM. 2 mM or 2.5 mM. In a more preferred embodiment, $SrCl_2$ and/or $BaCl_2$ and/or RbCl and/or CsCl and/or $CaCl_2$ is/are added to a final concentration of at least 400 mM to the product of step (d) before transfer onto the resin in step (e).

Optionally, precipitated material can be cleared from the product of step (d) by applying a centrifugal force, thereby forcing the insoluble precipitate to the bottom of the vessel used for centrifugation of the product of step (d). The cleared supernatant may then be applied onto the resin of step (e). In a preferred embodiment of the invention, the lysate of step (c) or step (d) is cleared from precipitates by centrifugation of the lysate before it is applied onto the resin in step (e), preferably by centrifugation at about 10000 g for 1 to 5 min.

Optionally, a chelating agent can be added to the biological sample at step (a). Chelating agents that bind metal ions are of special interest in nucleic acid stability. Many DNases use $Zn^{2+}$ as a cofactor for its activity and the use of a chelating agent inhibits those DNases by withdrawing the cofactor. In one embodiment, ethylenediaminetetraacetic acid (EDTA) and/or ethylene glycol-bis(β-aminoethyl ether)-N,N,N',N'-tetraacetic acid (EGTA) is/are used as a chelating agent. In a preferred embodiment, EDTA is used as a chelating agent. The concentration of the chelating agent preferably is at least 0.1 mM, 0.2 mM, 0.3 mM, 0.4 mM, 0.5 mM, 0.6 mM, 0.7 mM, 0.8 mM, 0.9 mM, 1 mM, at least 5 mM, at least 10 mM, at least 50 mM, at least 100 mM, at least 150 mM, at least 180 mM, at least 200 mM, at least 250 mM, at least 400 mM, at least 500 mM or at least 1 M. The chelating agent, such as EDTA, can be used at a concentration of about 10 mM, of about 1 mM or of about 0.1 mM. In preferred embodiments a chelating agent is added to the biological sample at step (a). Thus, the lysis performed in step (a) includes the presence of at least 0.1 mM, 0.6 mM, 1 mM or 2 mM of a chelating agent such as EDTA. It is also contemplated that the lysis performed in step (a) includes the presence of at least 20 mg/L, 25 mg/L, 30 mg/L, 35 mg/L, 40 mg/L, 45 mg/L, 50 mg/L, 55 mg/L, 60 mg/L, 65 mg/L, 70 mg/L, 75 mg/L, 80 mg/L, 90 mg/L, 100 mg/L, 200 mg/L, 300 mg/L, 400 mg/L, 500 mg/L or more of a chelating agent such as EDTA. It is also envisioned that more than one chelating agent is added to the biological sample at step (a).

It is contemplated that a detergent and DNA stabilizer as described herein can be added to the biological sample at step (a). Thus, ammonium chloride and SDS can be added to the biological sample at step (a). Additionally a chelating agent, wherein more than 0.1 mM or more than or about 1 mM or more than 20 mg/L chelating agent is used and/or a buffering substance can be added to the biological sample at step (a). For example, tartrate buffer, lithium dodecyl sulfate and ammonium chloride as well as EDTA can be added to the biological sample at step (a). Thus, about 50 mM tartaric acid, about 100 mM lithium dodecyl sulfate, about 155 mM ammonium chloride and at least 0.1 mM or at least 1 mM or more than 20 mg/L chelating agent, such as EDTA, can be added to the biological sample at step (a). It is envisioned that the lysis in step (a) is performed at a pH of about 8.3. It is further contemplated that the lysis is performed in the absence of $H_2SO_4$.

It is also envisioned that a detergent, a DNA stabilizer and a chelating agent as described herein can be added to the biological sample at step (a). For example, lithium dodecyl sulfate, ammonium chloride and EDTA can be added to the biological sample at step (a). Also SDS, EDTA and ammonium chloride can be added to the biological sample at step (a). Additionally, a buffering substance can be added to the biological sample at step (a).

For example, about 100 mM lithium dodecyl sulfate, about 155 mM ammonium chloride and at least 0.1 mM or at least 1 mM or at least 20 mg/L chelating agent can be added to the biological sample at step (a). Preferably, lysis is performed at a pH of about 8.3. Preferably, lysis is performed in the absence of $H_2SO_4$. For example, a buffering substance such as tartaric buffer can be added to the biological sample at step (a). E.g. 50 mM of tartaric acid can be added to the biological sample at step (a).

For example, about 100 mM SDS, about 150 mM ammonium chloride and at least 0.1 mM or at least 1 mM or more than 20 mg/L chelating agent can be added to the biological sample at step (a). It is contemplated that lysis is performed at a pH of about 8.0. Preferably, lysis is performed in the absence of $H_2SO_4$. For example, a buffering substance such as TRIS or TRIS/HCl. E.g. 50 mM of TRIS or TRIS/HCl can be added to the biological sample at step (a).

It is also contemplated that a detergent, a DNA stabilizer and a chelating agent, for example at least 1 mM chelating agent as described herein, can be added to the biological sample at step (a). For example, EDTA, SDS and ammonium chloride can be added to the biological sample at step (a). Additionally, the DNA stabilizer $CaCl_2$ can be added to the biological sample at step (a). For example, about 100 mM SDS, about 150 mM ammonium chloride and about 0.1-15 mM or 1 mM-15 mM (or at least 20 mg/L chelating agent such as EDTA (Na/EDTA) can be added to the biological sample at step (a). Optionally about 5 mM $CaCl_2$ and/or a buffering substance can additionally be added to the biological sample at step (a). It is envisioned that the lysis is performed in the absence of $H_2SO_4$.

In one embodiment of the invention, wherein a centrifugal force is used to facilitate the exiting of the flow through out of the resin, the centrifugation step is executed in step (e) after transfer of the product of step (d) onto the resin at 400 g to 3000 g for 0.5 to 5 min. This slow centrifugation increases the quality and amount of isolated nucleic acids, preferably DNA. Preferably the centrifugation step in step (e) is executed after transfer of the product of step (d) onto the resin at 400 g to 3000 g for 0.5 min to 5 min, more preferably for about 1 min.

To decrease the volume of the eluate, thereby increasing the concentration of the nucleic acids in the eluate, it is possible to apply a high centrifugal force to the resin, herein referred to as "preconditioning". In a preferred embodiment, the resin is centrifuged at least 1 min at at least 300 g before the lysate of step (d) is added onto the resin or the spin column in step (e).

In the following, embodiments comprising of different combinations of the above-mentioned obligatory and optional steps for the purification of the nucleic acids will be presented:

In one embodiment of the invention, the method for isolating nucleic acids is carried out, consisting of the following steps:
(a) optional lysis of a sample,
(b) optional heat incubation of said sample,
(c) enzymatic digestion of non-nucleic acid components in the product of step (a) or (b),
(d) heat inactivation of one or more enzyme(s) used in step (c),
(e) transfer of the product of step (d) onto a resin capable of retaining non-nucleic acid components, while the nucleic acids pass through the resin,
thereby purifying the nucleic acids.

In a preferred embodiment of the invention, the method for isolating nucleic acids is carried out, consisting of the following steps:
(a) lysis of a sample,
(b) heat incubation of said sample,
(c) enzymatic digestion of non-nucleic acid components in the product of step (a) or (b),
(d) heat inactivation of one or more enzyme(s) used in step (c),
(e) transfer of the product of step (d) onto a resin capable of retaining non-nucleic acid components, while the nucleic acids pass through the resin,
thereby purifying the nucleic acids.

In a preferred embodiment of the invention, the method for isolating nucleic acids is carried out, comprising the following steps:
(a) optional lysis of a sample,
(b) optional heat incubation of said sample,
(c) enzymatic digestion of non-nucleic acid components in the product of step (a) or (b), wherein one or more protease(s) is/are used and wherein the one or more protease(s) is/are selected from the group consisting of protease from *Bacillus licheniformis*, protease from *Bacillus* spec., protease from *Staphylococcus aureus*, protease from *Bacillus amyloliquefaciens*, protease from *Coprinus* spec. and protease from *Aspergillus oryzae*,
(d) heat inactivation of one or more enzyme(s) used in step (c),
(e) transfer of the product of step (d) onto a resin capable of retaining non-nucleic acid components, while the nucleic acids pass through the resin,
thereby purifying the nucleic acids.

In a preferred embodiment of the invention, the method for isolating nucleic acids is carried out, comprising the following steps:
(a) optional lysis of a sample, wherein a detergent is added to a final concentration of at least 20 mM SDS, at least 60 mM SDS, preferably at least 100 mM SDS, at least 150 mM SDS or at least 200 mM SDS and wherein ammonium salt(s) such as ammonium chloride and/or sulfate salt(s), preferably ammonium sulfate, is/are added, preferably wherein ammonium sulfate or ammonium chloride is added to a final concentration of at least 70 mM,
(b) optional heat incubation of said sample,
(c) enzymatic digestion of non-nucleic acid components in the product of step (a) or (b), wherein one or more protease(s) is/are used and wherein the one or more protease(s) is/are selected from the group consisting of protease from *Bacillus licheniformis*, protease from *Bacillus* spec., protease from *Staphylococcus aureus*, protease from *Bacillus amyloliquefaciens*, protease from *Coprinus* spec. and protease from *Aspergillus oryzae*,
(d) heat inactivation of one or more enzyme(s) used in step (c),
(e) transfer of the product of step (d) onto a resin capable of retaining non-nucleic acid components, while the nucleic acids pass through the resin,
thereby purifying the nucleic acids.

In a preferred embodiment of the invention, the method for isolating nucleic acids is carried out, comprising the following steps:
(a) optional lysis of a sample, wherein ammonium salt(s) such as ammonium chloride and/or sulfate salt(s), preferably ammonium sulfate, is/are added, preferably to a final concentration of at least 50 or at least 70 mM ammonium sulfate or ammonium chloride and wherein a detergent is added to a final concentration of at least 20 mM, at least 60 mM SDS, preferably of at least 100 mM SDS at least 150 mM SDS or at least 200 mM SDS,
(b) optional heat incubation of said sample,
(c) enzymatic digestion of non-nucleic acid components in the product of step (a) or (b), wherein one or more protease(s) is/are used and wherein the one or more protease(s) is/are selected from the group consisting of protease from *Bacillus licheniformis*, protease from *Bacillus* spec., protease from *Staphylococcus aureus*, protease from *Bacillus amyloliquefaciens*, protease from *Coprinus* spec. and protease from *Aspergillus oryzae*,
(d) heat inactivation of one or more enzyme(s) used in step (c),
(e) transfer of the product of step (d) onto a resin capable of retaining non-nucleic acid components, while the nucleic acids pass through the resin, wherein $SrCl_2$ and/or $BaCl_2$ has/have been added to a final concentration of at least 400 mM to the product of step (c) or (d) before transfer onto the resin of step (e),
thereby purifying the nucleic acids.

In a preferred embodiment of the invention, the method for isolating nucleic acids is carried out, comprising the following steps:
(a) optional lysis of a sample, wherein ammonium salt(s) such as ammonium chloride and/or sulfate salt(s) preferably ammonium sulfate, is/are added, preferably to a final concentration of at least 50 mM or at least 70 mM ammonium sulfate or ammonium chloride and wherein a detergent is added to a final concentration of at least 20 mM SDS, at least 60 mM SDS, preferably of at least 100 mM SDS, at least 150 mM SDS or at least 200 mM SDS,
(b) heat incubation of said sample,
(c) enzymatic digestion of non-nucleic acid components in the product of step (a) or (b), wherein one or more protease(s) is/are used and wherein the one or more protease(s) is/are selected from the group consisting of protease from *Bacillus licheniformis*, protease from *Bacillus* spec., protease from *Staphylococcus aureus*, protease from *Bacillus amyloliquefaciens*, protease from *Coprinus* spec. and protease from *Aspergillus oryzae*,
(d) heat inactivation of one or more enzyme(s) used in step (c),
(e) transfer of the product of step (d) onto a resin capable of retaining non-nucleic acid components, while the nucleic acids pass through the resin, wherein $SrCl_2$ and/or $BaCl_2$ has/have been added to a final concentration of at least 400 mM to the product of step (c) or (d) before transfer onto the resin of step (e), thereby purifying the nucleic acids.

In a preferred embodiment of the invention, the method for isolating nucleic acids is carried out, comprising the following steps:
(a) optional lysis of a sample, wherein ammonium salt(s) such as ammonium chloride and/or sulfate salt(s), preferably ammonium sulfate, is/are added, preferably to a final concentration of at least 50 mM or at least 70 mM ammonium sulfate or ammonium chloride and wherein a detergent is added to a final concentration of at least 20 mM SDS, at least 60 mM SDS, preferably of at least 100 mM SDS, at least 150 mM SDS or at least 200 mM SDS,
(b) heat incubation of said sample,
(c) enzymatic digestion of non-nucleic acid components in the product of step (a) or (b), wherein one or more protease(s) is/are used and wherein the one or more protease(s) is/are selected from the group consisting of protease from *Bacillus licheniformis*, protease from *Bacillus* spec., protease from *Staphylococcus aureus*, protease from *Bacillus amyloliquefaciens*, protease from *Coprinus* spec. and protease from *Aspergillus oryzae*,
(d) heat inactivation of one or more enzyme(s) used in step (c),
(e) transfer of the product of step (d) onto a resin capable of retaining non-nucleic acid components, while the nucleic acids pass through the resin, wherein $SrCl_2$ and/or $BaCl_2$ has/have been added to a final concentration of at least 400 mM to the product of step (c) or (d) before transfer onto the resin of step (e) and wherein the product of step (c) or (d) is added with a temperature between 60° C. and 95° C. onto the resin,
thereby purifying the nucleic acids.

In a preferred embodiment of the invention, the method for isolating nucleic acids is carried out, comprising the following steps:
(a) optional lysis of a sample, wherein ammonium salt(s) such as ammonium chloride and/or sulfate salt(s), preferably ammonium sulfate, is/are added, preferably to a final concentration of at least 50 mM or at least 70 mM ammonium sulfate or ammonium chloride and wherein a detergent is added to a final concentration of at least 20 mM SDS, at least 60 mM SDS, preferably of at least 100 mM SDS, at least 150 mM SDS or at least 200 mM SDS,
(b) optional heat incubation of said sample,
(c) enzymatic digestion of non-nucleic acid components in the product of step (a) or (b), wherein one or more protease(s) is/are used and wherein the one or more protease(s) is/are selected from the group consisting of protease from *Bacillus licheniformis*, protease from *Bacillus* spec., protease from *Staphylococcus aureus*, protease from *Bacillus amyloliquefaciens*, protease from *Coprinus* spec. and protease from *Aspergillus oryzae*,
(d) heat inactivation of one or more enzyme(s) used in step (c),
(e) transfer of the product of step (d) onto a resin capable of retaining non-nucleic acid components, while the nucleic acids pass through the resin, wherein $SrCl_2$ and/or $BaCl_2$ has/have been added to a final concentration of at least 400 mM to the product of step (c) or (d) before transfer onto the resin of step (e) and wherein the product of step (c) or (d) is added with a temperature between 60° C. and 95° C. onto the resin,
thereby purifying the nucleic acids.

Means for carrying out the method for isolating nucleic acids of this invention can be comprised in a kit. Such a kit comprises solutions for the lysis of a sample, enzymatic digestion, solution for precipitation of non-nucleic acid components and/or a resin for removal of non-nucleic acid components. Solutions for the lysis of a sample preferably comprise a stock solution of SDS and/or a stock solution of ammonium sulfate. The enzymes provided with this kit preferably comprise one or more enzyme(s) as defined herein, more preferably proteases. The choice of the one or more enzyme(s) may be optimized for the biological sample. Solutions for the precipitation of non-nucleic compounds comprise stock solutions of $BaCl_2$ or $SrCl_2$. Preferably, the resin is incorporated into a spin column and/or is a size exclusion resin. The kit may also comprise a lysis buffer as described herein.

The kit may also comprise components of a lysis buffer as described herein. The kit may thus comprise one or more of:
(a) solutions for the lysis of a sample, such as a lysis buffer as described herein;
(b) solutions for enzymatic digestion;
(c), solution for precipitation of non-nucleic acid components and/or
(d) a resin for removal of non-nucleic acid components.

The present invention also relates to lysis buffers comprising/consisting of a detergent and a DNA stabilizer as described herein. Thus, such a lysis buffer may comprise ammonium chloride and SDS. The lysis buffer may additionally comprise/consist of a chelating agent, wherein more than 0.1 mM or more than 1 mM or more than 20 mg/ml chelating agent is used and/or a buffering substance. For example, the lysis buffer may comprise a tartrate buffer, lithium dodecyl sulfate and ammonium chloride as well as EDTA. Thus, such a lysis buffer may comprise about 50 mM tartaric acid, about 100 mM lithium dodecyl sulfate, about 155 mM ammonium chloride and at least about 0.1 mM, 0.5 mM or 1 mM or at least 20 mg/L chelating agent, such as EDTA. Preferably, this lysis buffer has a pH of about 8.3. This buffer does preferably not comprise $H_2SO_4$.

The present invention also relates to lysis buffers comprising/consisting of a detergent, a DNA stabilizer and a chelating agent as described herein. For example, the lysis buffer may comprise a lithium dodecyl sulfate, ammonium chloride and EDTA. The lysis buffer may also comprise SDS, EDTA and ammonium chloride. These lysis buffers may additionally comprise/consist of a buffering substance.

Thus, such a lysis buffer may comprise about 100 mM lithium dodecyl sulfate, about 155 mM ammonium chloride and at least 0.1 mM or at least 1 mM or at least 20 mg/L chelating agent. Preferably, this lysis buffer has a pH of about 8.3. This buffer does preferably not comprise $H_2SO_4$. This lysis buffer may additionally comprise a buffering substance such as tartaric buffer. E.g. 50 mM of tartaric acid may be comprised in this lysis buffer.

Alternatively, such a lysis buffer may comprise about 100 mM SDS, about 150 mM ammonium chloride and at least 0.1 mM or at least 1 mM or at least 20 mg/L chelating agent. Preferably, this lysis buffer has a pH of about 8.0. This buffer does preferably not comprise $H_2SO_4$. This lysis buffer may additionally comprise a buffering substance such as TRIS or TRIS/HCl. E.g. 50 mM of TRIS or TRIS/HCl may be comprised in this lysis buffer.

The present invention also relates to lysis buffers comprising/consisting of a detergent, a DNA stabilizer and a chelating agent as described herein. For example, the lysis buffer may comprise EDTA, SDS and ammonium chloride. The lysis buffer may additionally comprise/consist of $CaCl_2$. Thus, such a lysis buffer may comprise about 100 mM SDS, about 150 mM ammonium chloride and about 0.1-15 mM or 1-15 mM (or more than 20 mg/L) chelating agent. Optionally, this lysis buffer may additionally comprise/consist of about 5 mM $CaCl_2$. Optionally, this lysis buffer may additionally comprise/consist of a buffering substance. This buffer does preferably not comprise $H_2SO_4$.

The lysis buffer of the present invention can comprise at least 20 mg/L, 25 mg/L, 30 mg/L, 35 mg/L, 40 mg/L, 45 mg/L, 50 mg/L, 55 mg/L, 60 mg/L, 65 mg/L, 70 mg/L, 75 mg/L, 80 mg/L, 90 mg/L, 100 mg/L, 200 mg/L, 300 mg/L, 400 mg/L, 500 mg/L or more of a chelating agent such as EDTA.

The lysis buffer of the present invention can be used in step (a) of the method of the present invention.

The present invention is further characterized by the following items:

1. Method for isolating nucleic acids from a sample, comprising the following steps:
    (a) optional lysis of said sample,
    (b) optional heat incubation of said sample,
    (c) enzymatic digestion of non-nucleic acid components in the product of step (a) or (b),
    (d) heat inactivation of one or more enzyme(s) used in step (c),
    (e) transfer of the product of step (d) onto a resin capable of retaining non-nucleic acid components, while the nucleic acids pass through the resin, thereby purifying the nucleic acids.
2. Method of item 1 wherein a detergent is added during step (a).
3. Method of item 1 or 2, wherein the detergent is SDS or LIDS.
4. Method of any of the preceding items, wherein the detergent is added to a final concentration of about 15 mM to 250 mM, 50 mM to 200 mM, preferably, 75-125 mM, most preferred in about 100 mM.
5. Method of any of the preceding items, wherein SDS is added to a final concentration of at least or about 60 mM SDS, preferably of at least or about 100 mM SDS, even more preferred at least or about 150 mM SDS, most preferred at least or about 200 mM SDS in the product of step (a).
6. Method of any of the preceding items, wherein LiDS is added to a final concentration of at least or about 60 mM LIDS, preferably of at least or about 100 mM LiDS, more preferred of at least or about 150 mM LiDS in the product of step (a).
7. Method of any of the preceding items, wherein a chelating agent is added at step (a), preferably the chelating agent is EDTA.
8. Method of any of the preceding items, wherein a chelating agent is added to a final concentration of at least 0.1 mM, 0.2 mM, 0.3 mM, 0.4 mM, 0.5 mM, 0.6 mM, 0.7 mM, 0.8 mM, 0.9 mM, 1 mM, 1.1 mM, 1.2 mM, 1.3 mM 1.4 mM, 1.5 mM, 2 mM, 2.5 mM, 3 mM, 3.5 mM 4 mM, 4.5 mM, 5 mM, 5.5 mM, 6 mM, 6.5 mM, 7 mM, 7.5 mM, 7.5 mM, 8 mM, 8.5 mM, 9 mM, 9.5 mM, 10 mM, 11 mM, 12 mM, 13 mM, 14 mM, 15 mM or more at step (a).
9. Method of any of the preceding items, wherein a chelating agent is added to a final concentration of about 10 mM or of about 0.1 mM or of about 1 mM.
10. Method of any of the preceding items, wherein a chelating agent is added to a final concentration of at least 20 mg/L, 25 mg/L, 30 mg/L, 35 mg/L, 40 mg/L, 45 mg/L, 50 mg/L, 55 mg/L, 60 mg/L, 65 mg/L, 70 mg/L, 75 mg/L, 80 mg/L, 90 mg/L, 100 mg/L, 200 mg/L, 300 mg/L, 400 mg/L, 500 mg/L or more.
11. Method of any of the preceding items, wherein a DNA stabilizer is added at step (a).
12. Method of any of the preceding items, wherein a DNA stabilizer is ammonium chloride and/or calcium chloride.
13. Method of any of the preceding items, wherein the DNA stabilizer is added to a final concentration of at least 25 mM, 50 mM, 75 mM, 100 mM, 125 mM, 150 mM, 175 mM, 200 mM, 225 mM 250 mM or more.
14. Method of any of the preceding items, wherein the DNA stabilizer is ammonium chloride which is added to a final concentration of about 150 mM or about 155 mM.
15. Method of any of the preceding items, wherein a buffer substance is added at step (a).
16. Method of any of the preceding items, wherein the buffer substance is selected from the group consisting of TRIS, such as TRIS-HCl, tartrate buffer, borate buffer, carbonate buffer, citrate buffer, HEPES, HPPS or any ammonia buffer, preferably the buffer substance is TRIS or tartrate buffer.
17. Method of any of the preceding items, wherein the buffer substance is added to a final concentration of at least 5 mM, 10 mM, 20 mM, 30 mM, 40 mM, 50 mM, 60 mM, 70 mM, 80 mM, 90 mM, 100 mM or more.
18. Method of any of the preceding items, wherein the buffer substance is TRIS and is added to a final concentration of about 50 mM at step (a).
19. Method of any of the preceding items, wherein the buffer substance is tartrate buffer and is added to a final concentration of about 50 mM at step (a).
20. Method of any of the preceding items, wherein $CaCl_2$ is added at step (a).
21. Method of any of the preceding items, wherein the $CaCl_2$ is added to a final concentration of at least 0.5 mM, 1 mM, 1.5 mM, 2 mM, 2.5 mM, 3 mM, 3.5 mM, 4 mM, 4.5 mM, 5 mM, 5.5 mM, 6 mM, 6.5 mM, 7 mM, 7.5 mM, 8 mM, 8.5 mM, 9 mM, 9.5 mM, 10 mM or more, preferably $CaCl_2$ is added to a final concentration of about 5 mM.
22. Method of any of the preceding items, wherein the lysis in step (a) is performed at a pH between about 5 and about 15, preferably between about 7 and about 13, more preferably between about 7 and about 10, most preferably between about 7 and about 9 or at a pH of about 8.
23. Method of any of the preceding items, wherein the heat incubation of step (b) is carried out at a temperature between 75° C. and 95° C. for 1 to 20 min, preferably for 2 to 10 min.
24. Method of any of the preceding items, wherein the heat incubation of step (b) is carried out at least 1 min, at least 5 min, at least 10 min, at least 15 min or at least 20 min.
25. Method of any of the preceding items, wherein one or preferably more enzyme(s) is/are used in step (c) for the enzymatic digestion, wherein the one or more enzyme(s) is/are lytic enzyme(s), preferably selected from the group consisting of proteases, lipases, cellulases, hydrolases, chitinases, amylases and glucanases, wherein hydrolases are not nucleases.
26. Method of any of the preceding items, wherein the enzymatic digestion of step (c) is carried out between 15° C. and 70° C. for 5 min to 120 min.
27. Method of any of the preceding items, wherein one or more protease(s) is/are used in step (c) and wherein the one or more protease(s) is/are selected from the group consisting of protease from *Bacillus licheniformis*, protease from *Bacillus* spec., protease from *Staphylococcus aureus*, protease from *Bacillus amyloliquefaciens*, protease from *Coprinus* spec. and protease from *Aspergillus oryzae*.
28. Method of any of the preceding items, wherein ammonium salt(s) and/or sulfate salt(s), preferably 28. ammonium sulfate, is/are added in step (a), preferably to a final concentration of at least 70 mM ammonium sulfate.
29. Method of any of the preceding items, wherein the product of step (d) is added with a temperature between 60° C. and 95° C. onto the resin at step (e).
30. Method of any of the preceding items, wherein $SrCl_2$ and/or $BaCl_2$ is/are added to a final concentration of at least 400 mM to the product of step (d) before transfer onto the resin in step (e).
31. Method of any of the preceding items, wherein said sample is a feces sample, blood sample, urine sample, tissue sample and/or body fluid sample.
32. Method of any of the preceding items, wherein said nucleic acid is DNA and/or RNA, preferably DNA.
33. Method of any of the preceding items, wherein a centrifugation step is executed in step (e) is executed after transfer of the product of step (d) onto the resin at 400 g to 3000 g for 0.5 min to 5 min, preferably for about 1 min.
34. Method of any of the preceding items, wherein said resin is a size-exclusion resin with exclusion limits in the range of 20 to 2000 bp of single and/or double stranded nucleotide strands.
35. Method of any of the preceding items, wherein said resin is incorporated into a spin column.
36. Method of any of the preceding items, wherein the resin is centrifuged at least 1 min at at least 300 g before the lysate of step (d) is added onto the resin or the spin column in step (e).
37. Method of any of the preceding items, wherein the lysate of step (c) or step (d) is cleared from precipitates by centrifugation of the lysate before it is applied onto the resin in step (e), preferably by centrifugation at about 10.000 g for 1 to 5 min.
38. Lysis buffer comprising a detergent, a DNA stabilizer and a chelating agent, wherein the chelating agent is present in a concentration of at least 0.1 or of at least 1 mM.
39. Lysis buffer comprising a detergent, a DNA stabilizer and a chelating agent, wherein the chelating agent is present in a concentration of at least 20 mg/L.
40. Lysis buffer comprising a detergent and one or more DNA stabilizer.
41. Lysis buffer comprising a detergent, a DNA stabilizer and buffer substance.
42. The lysis buffer of claim 37 or 38, wherein the detergent is SDS or LIDS.
43. The lysis buffer of any one of the preceding claims, wherein the detergent is present in a concentration of about 15 mM to 250 mM, 50 mM to 200 mM, preferably, 75-125 mM, even more preferred in about 100 mM, most preferred in a concentration of about 150 mM.
44. The lysis buffer of any of the preceding items, wherein SDS is present in the buffer in a concentration of at least 20 mM, at least 60 mM SDS, preferably of at least 100 mM SDS or at least 150 mM.
45. The lysis buffer of any of the preceding items, wherein LiDS is present in the buffer in a concentration of at least 20 mM, at least 60 mM LiDS, preferably of at least 100 mM LIDS or at least 150 mM.
46. The lysis buffer of any of the preceding items, wherein the DNA stabilizer is ammonium chloride.
47. The lysis buffer of any of the preceding items, wherein the DNA stabilizer such as ammonium chloride is added to a final concentration of at least 25 mM, 50 mM, 75 mM, 100 mM, 125 mM, 150 mM, 175 mM, 200 mM, 225 mM, 250 mM, 300 mM or more.
48. The lysis buffer of any of the preceding items, the DNA stabilizer is ammonium chloride is present in concentration of about 150 mM or about 155 mM in the lysis buffer.
49. The lysis buffer of any of the preceding items, wherein a chelating agent is present in a concentration of at least 0.1 mM, 0.2 mM, 0.3 mM, 0.4 mM, 0.5 mM, 0.6 mM, 0.7 mM, 0.8 mM, 0.9 mM, 1 mM, 1.1 mM, 1.2 mM, 1.3 mM 1.4 mM, 1.5 mM, 2 mM, 2.5 mM, 3 mM, 3.5 mM 4 mM, 4.5 mM, 5 mM, 5.5 mM, 6 mM, 6.5 mM, 7 mM, 7.5 mM, 7.5 mM, 8 mM, 8.5 mM, 9 mM, 9.5 mM, 10 mM, 11 mM, 12 mM, 13 mM, 14 mM, 15 mM or more at step (a).
50. The lysis buffer of any of the preceding items, wherein a chelating agent is present in a concentration of at least or about 0.1 mM, at least or about 1 mM or at least or about 10 mM.
51. The lysis buffer of any of the preceding items, wherein a chelating agent is present in a concentration of at least 20 mg/L, 25 mg/L, 30 mg/L, 35 mg/L, 40 mg/L, 45 mg/L, 50 mg/L, 55 mg/L, 60 mg/L, 65 mg/L, 70 mg/L, 75 mg/L, 80 mg/L, 90 mg/L, 100 mg/L, 200 mg/L, 300 mg/L, 400 mg/L, 500 mg/L or more.
52. The lysis buffer of any one of the preceding claims, wherein the chelating agent is EDTA, more preferably the chelating agent is Na-EDTA.
53. The lysis buffer of any of the preceding items, wherein the lysis buffer comprises ammonium chloride and SDS.
54. The lysis buffer of any of the preceding items, wherein the lysis buffer comprises lithium dodecyl sulfate and ammonium chloride.
55. The lysis buffer of any of the preceding items, wherein the lysis buffer further comprises a buffering substance.
56. The lysis buffer of any of the preceding items, wherein the buffer substance is selected from the group consisting of TRIS, such as TRIS-HCl, tartrate buffer, borate buffer, carbonate buffer, citrate buffer, HEPES, HPPS or any ammonia buffer, preferably the buffer substance is TRIS or tartrate buffer.
57. The lysis buffer of any of the preceding items, wherein the buffer substance is present in a concentration of at least 5 mM, 10 mM, 20 mM, 30 mM, 40 mM, 50 mM, 60 mM, 70 mM, 80 mM, 90 mM, 100 mM or more.
58. The lysis buffer of any of the preceding items, wherein the buffer substance is TRIS and is present in a concentration of about 50 mM at step (a).
59. The lysis buffer of any of the preceding items, wherein the buffer substance is tartrate buffer and is present in a concentration of about 50 mM at step (a).
60. The lysis buffer of any of the preceding items, wherein the lysis buffer comprises ammonium chloride, SDS and TRIS/HCl.
61. The lysis buffer of any of the preceding items, wherein the lysis buffer comprises lithium dodecyl sulfate, ammonium chloride and tartrate buffer.
62. The lysis buffer of any of the preceding items, further comprising $CaCl_2$.
63. The lysis buffer of any of the preceding items, wherein the $CaCl_2$ is present in a concentration of at least 0.5 mM, 1 mM, 1.5 mM, 2 mM, 2.5 mM, 3 mM, 3.5 mM, 4 mM, 4.5 mM, 5 mM, 5.5 mM, 6 mM, 6.5 mM, 7 mM, 7.5 mM, 8 mM, 8.5 mM, 9 mM, 9.5 mM, 10 mM or more, preferably $CaCl_2$ is present in a concentration of about 5 mM.

64. The lysis buffer of any of the preceding items, wherein the lysis buffer has a pH between about 5 and about 15, preferably between about 7 and about 13, more preferably between about 7 and about 10, most preferably between about 7 and about 9 or at a pH of about 8.
65. The lysis buffer of any of the preceding items, wherein the lysis buffer comprises tartrate buffer, lithium dodecyl sulfate, ammonium chloride as well as EDTA.
66. The lysis buffer of any of the preceding items, wherein the lysis buffer comprises lithium dodecyl sulfate, ammonium chloride and EDTA.
67. The lysis buffer of any of the preceding items, wherein the lysis buffer comprises SDS, EDTA and ammonium chloride.
68. The lysis buffer of any of the preceding items, wherein the lysis buffer comprises EDTA, SDS ammonium chloride and TRIS/HCl.
69. The lysis buffer of any of the preceding items, wherein the lysis buffer does not comprise $H_2SO_4$.
70. The lysis buffer of any of the preceding items, wherein the lysis buffer comprises $Mg^{2+}$.
71. The lysis buffer of any of the preceding items, wherein the lysis buffer consists of tartaric acid, LiDS and ammonium chloride.
72. The lysis buffer of any of the preceding items, wherein the lysis buffer consists of tartaric acid, LiDS, ammonium chloride and EDTA.
73. The lysis buffer of any of the preceding items, wherein the lysis buffer consists of SDS, ammonium chloride and EDTA.
74. The lysis buffer of any of the preceding items, wherein the lysis buffer consists of TRIS/HCl, ammonium chloride, SDS and $CaCl_2$.
75. The lysis buffer of any of the preceding items, wherein the lysis buffer consists of TRIS/HCl, ammonium chloride, SDS, $CaCl_2$ and EDTA.
76. The lysis buffer of any of the preceding items, wherein the lysis buffer consists of TRIS/HCl, ammonium chloride, SDS, and Na-EDTA.
77. The lysis buffer of any of the preceding items, wherein the lysis buffer consists of 50 mM TRIS/HCl, 150 mM ammonium chloride, 100 mM SDS, and about 0.1 or about 1 mM Na-EDTA.
78. The lysis buffer of any of the preceding items, wherein the lysis buffer consists of 50 mM TRIS/HCl, 150 mM ammonium chloride, 100 mM SDS, and about 0.1 or about 1 mM Na-EDTA and has a pH of about 8.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

All publications and patents cited in this disclosure are incorporated by reference in their entirety. To the extent, the material incorporated by reference contradicts or is inconsistent with this specification, the specification will supersede any such material.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein, any of the terms "comprising", "consisting essentially of" and "consisting of" may be replaced with either of the other two terms.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

When used herein, the term "about" is understood to mean that there can be variation in the respective value or range (such as pH, concentration, percentage, molarity, number of amino acids, time etc.) that can be up to 5%, up to 10%, up to 15% or up to and including 20% of the given value. For example, if a formulation comprises about 5 mg/ml of a compound, this is understood to mean that a formulation can have between 4 and 6 mg/ml, preferably between 4.25 and 5.75 mg/ml, more preferably between 4.5 and 5.5 mg/ml and even more preferably between 4.75 and 5.25 mg/ml, with the most preferred being 5 mg/ml. As used herein, an interval which is defined as "(from) X to Y" equates with an interval which is defined as "between X and Y". Both intervals specifically include the upper limit and also the lower limit. This means that for example an interval of "5 mg/ml to 10 mg/ml" or "between 5 mg/ml and 10 mg/ml" includes a concentration of 5, 6, 7, 8, 9, and 10 mg/ml as well as any given intermediate value.

EXAMPLES

Materials and Methods

Described herein are materials needed for nucleic acid extraction and a general method for the isolation of nucleic acids. Changes indicated in the Examples supersede the general method. This general method is suitable for up to 10 mg fresh, frozen or stabilized tissue sample per preparation, but not for more than 5 mg spleen tissue.

Materials

This list shows materials needed for the isolating nucleic acids:

Microcentrifuge with rotor for 1.5 ml and 2 ml reaction tubes set to 650 g

For fastest performance: Thermomixer, capable of heating to 60° C. and 80° C. with agitation (800-1500 rpm), pre-heated to 60° C. or alternatively: heating block, pre-heated to 60° C.

Vortex mixer

One reaction tube (1.5 ml) per sample for the lysis step, preferably safe-lock

One reaction tube (2 ml) per sample for column preparation.

One reaction tube (1.5 ml) per sample for elution and collection of the purified genomic DNA Pipets for 10 µl and up to 200 µl, corresponding pipet tips Size exclusion chromatography column: Spin columns filled with 700 µl of Sephacryl S-400 in TRIS buffer, pH 7 (GE)

Lysis buffer: 25 mM TRIS buffer, pH 7; 70 mM SDS; 90 mM $(NH_4)_2SO_4$

Clearing solution: 2 M $SrCl_2$

Protector solution: 100 mM EDTA

Proteases were obtained from QIAGEN (Table 2, lines 2-4), Sigma-Aldrich (Table 2, lines 5-10, 13-17, 19-20) or CLEA technologies (19-20). Other proteases were self-made.

Isolation of Nucleic Acids

In the following, a method for isolating DNA is described. It consists of the steps lysis and sample clearing, column preparation, and clearing and purification.

Lysis and Sample Clearing

Cut sample (max. 10 mg tissue, 5 mg spleen) into small pieces and place in a 1.5 ml tube Add 80 µl Lysis Buffer, 3 µl Protease, 2 µl RNase A solution Incubate 15-30 min at 60° C. with agitation (30-60 min, vortex).

Incubate 10 min at 80° C. with agitation (10 min, vortex).

Column Preparation (During 80° C. Incubation)

If air is present in the column, remove by vortexing.

Centrifuge 1 min at 650×g.

Place the column in a 1.5 ml tube.

Clearing and Purification

Add 20 µl Clearing Solution and vortex.

Centrifuge 3 min at highest speed.

Transfer 100 µl lysate: vertically through cap, pipet slowly into the column, or pipet slowly on resin bed.

Centrifuge 1 min at 650×g

The eluate contains the isolated DNA and can be further processed. Resulting DNA was analyzed by agarose gel electrophoresis.

In the following, a more detailed description of the isolation of DNA is described:

Lysis and Clearing

1. Prepare 80 µl Lysis Buffer and 3 µl protease per sample and mix by flicking or vortexing. If working with more than two samples, prepare a pre-mix with a final volume that is 10% larger than required for the number of samples (see examples in table 1 below).

TABLE 1

|  | No of samples | | | |
|---|---|---|---|---|
|  | 1 | 6 (+10%) | 12 (+10%) | 20 (+10%) |
| Tissue Lysis Buffer (µl) | 80 | 528 | 1056 | 1760 |
| TurboLyse Protease (µl) | 3 | 20 | 40 | 66 |
| Protector Solution (µl) | 1 | 7 | 13 | 22 |
| Sum (µl) | 84 | 555 | 1109 | 1848 |

2. Cut up to 10 mg tissue (5 mg for spleen only) into small pieces and place in a 1.5 ml reaction tube. Keep fresh or frozen samples cold until all samples are prepared. For stabilized tissue samples only: rinse them briefly with water to remove traces of stabilization solution before adding samples to the sample tube.

3. Add 85 µl of the pre-mix from step 1 to each sample.
4. Incubate samples in a thermomixer at 60° C. with agitation at full speed for 30 min. Alternatively, incubate on a heating block for 60 min and pulse-vortex 3 times during lysis. If samples are not completely lysed after the time period described above, continue with the next step. Residual cellular debris will not interfere with the purification performance. Note: For some tissue types, lysis is already complete after 15 min. No remaining tissue is visible and the overall time can be shortened accordingly.
5. Increase the temperature to 80° C. and continue the incubation as described above for an additional 10 min. Meanwhile, proceed with "Column Preparation" (below).

Column Preparation

6. Place a Spin Column into a 2 ml reaction tube. Note: If air is present in the column: remove by vortexing briefly. Snap off the bottom closure of the Spin Column. Important: Loosen the screw cap of the spin column a half turn to avoid yield reduction due to generation of a vacuum. Place back the column into the 2 ml collection tube.
7. Centrifuge for 1 minute at 650 g. See section "Materials and equipment needed" above for details. Discard the 2 ml reaction tube containing the flow through.
8. Place the prepared spin column into a new 1.5 ml reaction tube for elution of the sample and both together in a rack. Continue with "Purification" (below).

Purification

9. After having performed step 5, add 20 µl Clearing Solution and 2 µl RNase A to each sample. Vortex 3 s to mix.
10. Centrifuge for 3 min at maximum speed.
11. Aspirate the supernatant (90-110 µl lysate containing the DNA) and transfer to the prepared column from step 8 as described below.

Open cap and pipet the lysed sample slowly onto the middle of the resin bed of the prepared Spin Column. Close cap. Important: Loosen the screw cap of the spin column a half turn to avoid yield reduction.

12. Centrifuge 1 minute at 650 g. The purified genomic DNA (90-100 µl; 10 mM Tris.Cl, pH 7.6) flows through the column into the 1.5 ml elution tube. Discard the spin column.
13. The eluted genomic DNA can be used immediately or stored at 4° C. or −20° C.

Example 1: Influence of Heat Inactivation Step, EDTA and High SDS Concentrations in Lysis Buffer To elucidate the role of heat inactivation of nucleases, EDTA and high SDS concentrations in the lysis buffer, different conditions for the lysis and heat inactivation step have been compared. The following table shows the different conditions used:

TABLE 2

| Conditions used in Example 1 | | | |
|---|---|---|---|
| No | SDS [mM] | EDTA [mM] | Heat inactivation |
| 1 | 100 |  | No |
| 2 | 75 |  | No |
| 3 | 50 |  | No |
| 4 | 100 |  | 10 min @ 90° C. |
| 5 | 75 |  | 10 min @ 90° C. |
| 6 | 50 |  | 10 min @ 90° C. |
| 7 | 100 | 11.1 mM | No |

TABLE 2-continued

Conditions used in Example 1

| No | SDS [mM] | EDTA [mM] | Heat inactivation |
|---|---|---|---|
| 8 | 75 | 11.1 mM | No |
| 9 | 50 | 11.1 mM | No |
| 10 | 100 | 11.1 mM | 10 min @ 90° C. |
| 11 | 75 | 11.1 mM | 10 min @ 90° C. |
| 12 | 50 | 11.1 mM | 10 min @ 90° C. |

The sample was a feces sample. After lysis and heat incubation, proteolytic digestion and purification on a resin followed. The obtained DNA was analyzed on an agarose gel. The results, depicted in FIG. 1 showed that a heat incubation step (lanes 4-6 and 10-12) are beneficiary and yields in higher amounts of isolated DNA. In addition, high SDS concentrations (lanes 4 and 10) are beneficial compared to lower concentrations. A further result was that the addition of EDTA increased the resulting amount of DNA (lanes 7-12).

Example 2: Influence of Ammonium Sulfate

To test the influence of high $(NH_4)_2SO_4$ concentrations, different conditions for the $(NH_4)_2SO_4$ concentration during lysis were tested. Here, a blood sample was analyzed with the conditions as shown in the following table:

TABLE 3

SDS and ammonium sulfate concentrations used in example 2.

| | Parameters | Protease [µl] |
|---|---|---|
| 1 | 20 mM SDS; 90 mM $(NH_4)_2SO_4$ | 1 |
| 2 | 20 mM SDS; 200 mM $(NH_4)_2SO_4$ | 1 |
| 3 | 20 mM SDS; 90 mM $(NH_4)_2SO_4$ | 3 |
| 4 | 20 mM SDS; 200 mM $(NH_4)_2SO_4$ | 3 |
| 5 | 50 mM SDS; 90 mM $(NH_4)_2SO_4$ | 1 |
| 6 | 50 mM SDS; 200 mM $(NH_4)_2SO_4$ | 1 |
| 7 | 50 mM SDS; 90 mM $(NH_4)_2SO_4$ | 3 |
| 8 | 50 mM SDS; 200 mM $(NH_4)_2SO_4$ | 3 |
| 9 | 20 mM SDS; 90 mM $(NH_4)_2SO_4$ | 1 |
| 10 | 20 mM SDS; 200 mM $(NH_4)_2SO_4$ | 1 |
| 11 | 20 mM SDS; 90 mM $(NH_4)_2SO_4$ | 3 |
| 12 | 20 mM SDS; 200 mM $(NH_4)_2SO_4$ | 3 |
| 13 | 50 mM SDS; 90 mM $(NH_4)_2SO_4$ | 1 |
| 14 | 50 mM SDS; 200 mM $(NH_4)_2SO_4$ | 1 |
| 15 | 50 mM SDS; 90 mM $(NH_4)_2SO_4$ | 3 |
| 16 | 50 mM SDS; 200 mM $(NH_4)_2SO_4$ | 3 |

The lysis step was carried out at 60° C. for 30 min, followed by a heat incubation step at 80° C. for 10 min. Also, different volumes of the protease were used. The DNA was then isolated by a resin and the resulting eluate was subjected to a gel electrophoresis. The results, shown in FIG. 2, show a clear pattern for a positive influence of $(NH_4)_2SO_4$. In every lane with an odd (1, 3, 5, 7, 9, 11, 13, 15) number with a lower concentration of ammonium sulfate, there is less DNA recovered in comparison to the lanes with an even number (2, 4, 6, 8, 10, 12, 14, 16), where higher concentrations of ammonium sulfate were used. In addition, as SDS concentrations have also been varied in this example, there is again a clear indication for a positive influence of higher SDS concentration. Lanes 5-8 and 13-16 show a much higher recovery of DNA compared to the other lanes with lower recovery rates.

Example 3: Influence of New Proteases

As outlined in the description, the enzymatic digestion of non-nucleic acid components is essential for a successful purification of nucleic acids. In this example, different proteases are compared. A blood sample was lysed and subsequently subjected to a proteolytic digestion. The proteolytic digestion was carried out for 30 min at 60° C. The following table shows the different proteases that have been used in this example:

TABLE 4

Proteases used in example 3

| No | Protease, 30 min 60° C. | Volume [µl] |
|---|---|---|
| 1 | No protease | 10 |
| 2 | Qiagen Protease | 10 |
| 3 | Qiagen Protease | 20 |
| 4 | Qiagen Protease K | 10 |
| 5 | *Bacillus licheniformis* version 1 | 10 |
| 6 | *Bacillus licheniformis* version 1 | 10 |
| 7 | *Bacillus licheniformis* version 1 | 20 |
| 8 | *Bacillus licheniformis* version 1 | 30 |
| 9 | *Bacillus licheniformis* version 1 | 10 |
| 10 | *Bacillus licheniformis* version 1 | 20 |
| 11 | *Bacillus amyloliquefaciens* version 205 | 10 |
| 12 | *Bacillus amyloliquefaciens* version 205 | 20 |
| 13 | *Bacillus licheniformis*, version 2 | 10 |
| 14 | *Bacillus licheniformis*, version 2 | 20 |
| 15 | *Bacillus* spec., | 10 |
| 16 | *Bacillus licheniformis* version 3 | 10 |
| 17 | *Staphylococcus aureus* V8 | 10 |
| 18 | *Bacillus amyloliquefaciens* version JH | 10 |
| 19 | *Bacillus amyloliquefaciens* version 1 | 10 |
| 20 | *Aspergillus oryzae* | 10 |

After the proteolytic digestion, DNA was isolated and analyzed by agarose gel electrophoresis. The results are shown in FIG. 3. As obvious from lane 1, no protease leads to almost no recovery of DNA, supporting the important role of proteases. Lanes 2-4 show proteases known in prior art. They lead to a recovery of some, but not much DNA. Lanes 5-10 show different concentrations and batches of the protease from *Bacillus licheniformis*, version 1. They lead to a recovery rate similar to proteases of the prior art. By using other proteases, shown in lanes 11-20, the recovery rate could be greatly increased. This shows the importance of the beneficial choice of protease.

The invention claimed is:

1. A method for isolating nucleic acids from a sample, comprising the following steps:
    (a) lysis of said sample in the presence of EDTA and 50-100 mM SDS,
    (b) enzymatic digestion of non-nucleic acid components in the product of step (a) at a temperature in the range of 55 to 65° C.,
    (c) heat inactivation of one or more enzyme(s) used in step (b) at a temperature between 80-95° C.,
    (d) transfer of the product of step (c) onto a resin capable of retaining non-nucleic acid components, while the nucleic acids pass through the resin, thereby purifying the nucleic acids.

2. The method of claim 1, wherein the enzymatic digestion of step (b) is carried out for 1 to 240 min, optionally for 5 to 120 min.

3. The method of claim 1, wherein the enzymatic digestion of step (b) is carried out for at least 1 min, at least 5 min, at least 10 min, at least 15 min or at least 20 min.

4. The method of claim 1, wherein one or more enzyme(s) is/are used in step (b) for the enzymatic digestion, wherein the one or more enzyme(s) is/are lytic enzyme(s), optionally selected from the group consisting of proteases, lipases, cellulases, hydrolases, chitinases, amylases and glucanases, wherein hydrolases are not nucleases.

5. The method of claim 1, wherein the enzymatic digestion of step (b) is carried out at 60° C. for 5 min to 120 min, preferably for 30 mins.

6. The method of claim 1, wherein one or more protease(s) is/are used in step (b) and wherein the one or more protease(s) is/are selected from the group consisting of protease from *Bacillus licheniformis*, protease from *Bacillus* spec., protease from *Staphylococcus aureus*, protease from *Bacillus amyloliquefaciens*, protease from *Coprinus* spec. and protease from *Aspergillus oryzae*.

7. The method of claim 1, wherein ammonium salt(s) is/are added in step (a), optionally to a final concentration of at least 5 mM.

8. The method of claim 1, wherein $SrCl_2$ and/or $BaCl_2$ is/are added to a final concentration of at least 400 mM to the product of step (c) before transfer onto the resin in step (d).

9. The method of claim 1, wherein said sample is a feces sample, blood sample, urine sample, tissue sample and/or body fluid sample.

10. The method of claim 1, wherein said nucleic acid is DNA and/or RNA, optionally DNA.

11. The method of claim 1, wherein a centrifugation step is executed in step (d) after transfer of the product of step (c) onto the resin at 400 g to 3000 g for 0.5 min to 5 min, optionally for about 1 min.

12. The method of claim 1, wherein said resin is a size-exclusion resin with exclusion limits in the range of 20 to 2000 bp of single and/or double stranded nucleotide strands.

13. The method of claim 1, wherein said resin is incorporated into a spin column.

14. The method of claim 13, wherein the resin is centrifuged at least 1 min at least 300 g before the lysate of step (c) is added onto the resin or the spin column in step (d).

15. The method of claim 1, wherein the lysate of step (b) or step (c) is cleared from precipitates by centrifugation of the lysate before it is applied onto the resin in step (d), optionally by centrifugation at about 10.000 g for 1 to 5 min.

16. The method of claim 1, wherein said sample comprises cells and/or cell-free nucleic acids from bacteria, virus, protozoa, chromista, fungi, plants and/or animals.

17. The method of claim 1, wherein SDS and/or LiDS is used in the lysis step (a).

18. The method of claim 17, wherein $SrCl_2$, $BaCl_2$, RbCl, CsCl, $CaCl_2$) is/are added to the product of step (c) before the transfer onto the resin of step (d).

19. The method of claim 1, wherein $SrCl_2$, $BaCl_2$, RbCl, CsCl, $CaCl_2$) is/are added to the product of step (c) before the transfer onto the resin of step (d).

* * * * *